United States Patent [19]
Zetterquist

[11] Patent Number: 5,102,715
[45] Date of Patent: Apr. 7, 1992

[54] LABEL WITH BACTERICIDAL AGENT FOR PROLONGING THE LIFE OF CUT FLOWERS

[76] Inventor: Lars Zetterquist, Ostgötavägen 5, S-222 25 Lund, Sweden

[21] Appl. No.: 623,259

[22] Filed: Dec. 5, 1990

Related U.S. Application Data

[63] Continuation of Ser. No. 381,672, Jul. 14, 1989, abandoned.

[30] Foreign Application Priority Data

Jan. 23, 1987 [SE] Sweden ................................ 8700259

[51] Int. Cl.$^5$ .................... B32B 3/10; A01N 3/02; A01N 25/34; A01G 5/06
[52] U.S. Cl. .................................... 428/137; 428/131; 428/520; 428/480; 428/907; 428/195; 428/192; 428/343; 428/345; 428/351; 428/354; 428/341; 428/913; 428/404; 428/409; 428/412; 428/138; 71/68; 47/1.01; 47/7; 47/55
[58] Field of Search ............... 428/131, 520, 480, 907, 428/913, 138, 195, 192, 343, 345, 351, 354, 341; 71/68; 47/1.01, 7, 55; 424/404, 409, 412

[56] References Cited

U.S. PATENT DOCUMENTS

| | | | |
|---|---|---|---|
| 4,160,335 | 7/1979 | Von Kohorn et al. | 428/907 |
| 4,167,832 | 9/1979 | Zetterquist et al. | 47/1.01 |
| 4,181,752 | 1/1980 | Martens et al. | 428/483 X |
| 4,225,679 | 9/1980 | Pilato | 71/68 |
| 4,237,114 | 12/1980 | Cardarelli | 424/83 |
| 4,256,773 | 3/1981 | Itoga et al. | 71/68 |
| 4,289,815 | 9/1981 | Lee | 428/500 X |
| 4,418,038 | 11/1983 | Theeuwes | 514/411 |
| 4,500,339 | 2/1985 | Young et al. | 424/78 |
| 4,552,752 | 11/1985 | Amick | 424/419 |
| 4,557,980 | 12/1985 | Hodnett, III | 428/336 |
| 4,818,610 | 4/1989 | Zimmerman et al. | 428/345 |

Primary Examiner—Ellis P. Robinson
Assistant Examiner—William P. Watkins, III
Attorney, Agent, or Firm—Ladas & Parry

[57] ABSTRACT

An article for preserving fresh cut flowers placed in water, which is in the form of a label applicable to one or more stalks of the cut flowers. The label has a water insoluble carrier layer, a coat of material applied to the carrier layer containing an active material and a barrier layer to water applied to the coat. The active material comprises at least one active substance which sets free bactericidal and/or bacterial inhibiting agents in the presence of water. The barrier layer in cooperation with the carrier layer regulates the size of the total contact surface of the water with the active material and consequently the release time for the active substance when the label is immersed into the water.

18 Claims, 1 Drawing Sheet

LABEL WITH BACTERICIDAL AGENT FOR PROLONGING THE LIFE OF CUT FLOWERS

This is a continuation of copending application Ser. No. 07/381,672 filed on July 14, 1989 is now abandoned and International Application PCT/SE88/00018 filed on Jan. 22, 1988 and which designated the U.S."

FIELD OF THE INVENTION

The present invention relates to a means for prolonging the life of cut flowers standing in water. The means is in the form of a label which comprises a water-insoluble carrier layer and a coat applied to the same, the coat containing an active material with at least one substance setting free bactericidal and/or bacterial inhibiting agents in the presence of water.

BACKGROUND AND PRIOR ART

A plant contains a network of ducts for the transport from the roots to the shoot of water and substances dissolved therein. When a flower-stalk is cut off these ducts are opened, so that during the remaining life of the flower the water, which normally comes from the roots and which is constantly supplied to leaves and flowers so that they should not wilt, now has to be absorbed through the cut wound formed. It is of greatest importance for the keeping the quality of cut flowers, therefore, that the ducts in the stalks should be kept open as long as possible after the cutting, so as to make possible this transport of water and of substances possibly dissolved in the water. Choking up of the ducts may occur through bacteria and algae penetrating into them or through scar substances which are formed by the plants inside the ducts, or through the actual cut surface receiving a coating of microorganisms.

The impaired water absorption of cut flowers which have been placed in a container as a rule causes them to wilt much earlier than if they had been allowed to remain on the plant. Through frequency cutting off of the flower stalks and daily changing of the water, the life can be prolonged to some extent, but since such measures necessitate both care and effort, they are frequently neglected. By using a so-called preservative agent which is dissolved in the vase water it is possible, however, without too much effort to prolong the life. In this way one of the causes for the early wilting and death of the flowers is acted upon, namely the aforementioned choking up of the duct.

In cut flowers which have been cut off from the mother plant the nutrient reserve (consisting primarily of sugar) in leaves and flowers rapidly becomes exhausted, whereupon the flowers wilt. If this starvation can be prevented in that a nutrient substance, e.g. usually sugar, is supplied from the outside via the water, an appreciable prolongation of life becomes feasible. However, the possibility of a supply of sugar from the outside too will depend, of course, on being able to keep open the ducts in the stalks. Since a sugar solution is an excellent substrate also for bacterial growth, the addition of sugar to the base water entails the risk, though, that stoppage of the ducts is increased. This too can be prevented by the addition of a so-called preservative agent (bactericidal agent) to the water as a result of which the duct openings remain open and nutrient supplied to the water can be absorbed by the cut flowers.

The presence of large quantities of bacteria in vases with cut flowers has been established. A bacteria count of up to $10^{13}$ ml$^{-1}$ has been reported. Attention has been drawn in particular to the occurrence of so-called gram-negative pathogens in flower vases in a hospital environment.

In order to prolong the life of cut flowers U.S. Pat. No. 4,167,832 discloses a coat or a label which contains active material for directly contacting the water so that on immersion of the label in the water a reaction is started by which at the entire surface of the coat chlorine is released from the layer. The quantity of chlorine which at any given time is present in the water is determined partly by the rate of reaction, partly by the consumption and evaporation of chlorine from the liquid surface. On application of the technique described in the patent specification it is found that when the label is immersed in the water, a very rapid liberation of chlorine is initiated which leads to a rapidly increasing chlorine concentration in the water. According to the patent specification this agrees with the effect aimed at, since it is the intention through a rapidly increased concentration of chlorine to kill quickly all bacteria in the water and prevent thereby any stopping up of the liquid and nutrient duct endings at the cut surface.

A serious disadvantage associated with release of a large quantity of chlorine into the vase water during a very short period is that the high chlorine concentration which arises in the water causes damage to cut flowers with sensitive foliage and sensitive stalks.

It is a further disadvantage that the active agent is consumed relatively quickly which in turn leads to premature dimination of the chlorine concentration of the water, that is to say the flowers wilt earlier than would be the case with a better distribution in the release time of the chlorine.

The label in accordance with the aforesaid patent has the further disadvantage that the active substance is set free when the label comes into contact with water during transport or storage. When the active substance is chlorine, a strong smell of chlorine will ensue. On skin contact with the label, skin irritations easily can occur which may cause problems for persons frequently handling the product, e.g. employees in flower shops. There is also a risk that clothes may be damaged on coming into contact.

SUMMARY OF THE INVENTION

It is the object of the invention to reduce to a substantial degree the abovementioned problems and to provide a means which makes its possible to keep the flowers fresh in the water for a longer time than has been possible hitherto.

The novelty of the invention consists essentially in that the coat of active material is surrounded on each of its two sides by at least one substantially water-impermeable layer and that between the water-impermeable layers located closest to the coat, and/or through passages provided in the layer, regions for contact of the water with the active material are formed.

In accordance with a preferred embodiment of the invention a coat of active material includes a substance which sets free chlorine, preferably sodium dichloroisocyanurate.

In accordance with a preferred embodiment the water-impermeable barrier layer is formed by a lacquer based on at least one acrylic compound. This is selected from the group consisting of acrylate derivatives, diacrylate derivatives, triacylate derivative and acrylo-epoxide compounds, the lacquer containing moreover a photoinitiator which initiates the hardening of the lacquer under the influence of UV-light.

BRIEF DESCRIPTION OF THE FIGURES OF THE DRAWING

The invention will be described in greater detail with reference to the drawing, wherein.

DETAILED DESCRIPTION

Figure 1:
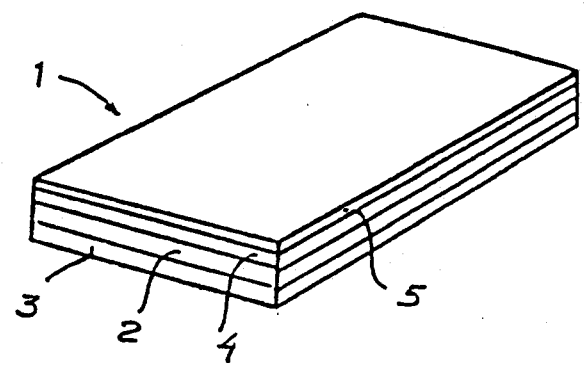
FIG. 1 shows schematically an article in accordance with the invention.

In FIG. 1 is shown schematically an embodiment of the invention where an article in the form of a label 1 comprises a carrier layer 2, which in accordance with a preferred embodiment consists of a water-insoluble and, substantially, water-impermeable flexible material, preferably a plastic material, e.g. polyvinyl chloride, polypropylene or similar material. The carrier layer as a rule is relatively thin, and a thickness of approx. 0.1 mm has proved to be sufficient. Alternatively, the carrier layer consists of some other material with a certain capacity of allowing the passage of liquid or the drawing up or absorbing of the same, e.g. paper or cardboard.

The carrier layer of the label is covered on its upper side with a coat 4 which contains an active material containing at least one active substance which releases bactericidal and/or bacterial inhibiting agents in the presence of moisture or water. Such a preferred active substance, which is used in an embodiment of the invention, is sodium dichloroisocyanurate. The coat 4 comprises further a carrier material for the active material in the form of a plastic binder. On application, the plastic binder and the active material are mixed to from a paste with which the solid carrier layer 2.

The label is shown in FIG. 1 in an embodiment where the underside of the carrier layer, and consequently of the label, is covered with an adhesive or a binder layer 3. The binder layer in accordance with a preferred embodiment consists of a rubber-based binder, e.g. that which is known in the trade as Beiersdorb B4. In certain applications the binder layer consists of a water-impermeable material. This latter embodiment is used especially when the carrier layer is water-permeable and the binder layer is used in order to protect the surface of the carrier layer from contact with the water, which otherwise easily could pass through the carrier layer and make contact with the coat 4 comprising active material.

The coat 4 which contains active material is coated on its upper side with a layer 5, referred to hereinafter as barrier layer 5, of substantially water-impermeable material. When the label is lowered into the water, the barrier layer prevents the water from coming into contact with the surface of the coat 4. Through the placement and design of the barrier layer and the carrier layer, alternatively of the binder layer, alone the extent of the surface of the coat 4 which makes contact with the water is, and consequently the quantity of bactericidal agent which on each occasion is released. Active substance diffuses out continuously, but at a rate diminishing in time, from the surfaces which are not covered by layers representing barriers against the water. In certain applications a water-permeable layer is arranged between the carrier layer 2 and the coat 4 and/or between the coat 4 and the barrier layer 5 in order to improve the release of active substance from central parts of the label.

It is evident from FIG. 1 that in the embodiment shown in the Figure the traverse edge surfaces of the label are devoid of protective layers. In other embodiments where it is desired to reduce the exposed contact surface, at least some edges are coated wholly or partly with a protective layer. In certain embodiments the barrier layer 5 does not cover the whole coat, but leaves regions adjoining the edges of the label uncovered. In yet other embodiments the exposed contact surface is increased by means of one or several holes in the label.

The embodiment where all edges are without protective layers has advantages from a point of view of manufacture, since the individual labels can be punched out from a larger plate containing the coat 4 with active material as well as all the layers surrounding the coat.

Figure 2:
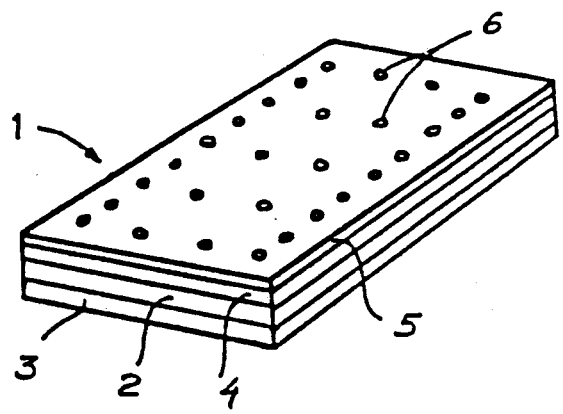
FIG. 2 shows an alternative embodiment of the article in accordance with the invention, and FIG. 3 graphically shows a curve diagram with the results of comparative experiments.

FIG. 2 shows an embodiment of the invention according to which the barrier layer 5 is provided with passage 6 which allow direct contact between the coat 4 of active material and the environment. As is evident from the Figure the number of passages, and consequently the contact surface of the active material per surface unit, in certain embodiments is greater near the edges of the label. This distribution of passages is chosen in applications where there is a need for a more rapid release of bactericidal means as soon as the label has been placed in the water and for a complete release of active substance from the coat 4 of active material within a certain time. In the Figure the passages are shown as round holes, but alternative designs of the passages, e.g. slots, perforations etc., of course, are likewise within the concept of the invention. Although in FIG. 2 passages are only shown on the barrier layer, in certain applications the carrier layer and/or the binder layer too are also provided with passages. The latter alternative relates in particular to applications where the binder layer 3 does not permit the passage of water and of bactericidal and/or bacterial inhibiting means. This latter embodiment, of course, is feasible only in cases where The label is immersed into the water or in applications where the flowers tolerate the high concentrations of bactericidal and/or bacterial inhibiting agents which occur in connection with passages in the carrier layer.

Prior to use, the label is stored appropriately on a protective foil to which the label is fixed detachably, with its binder layer 3 lying against the protective foil.

According to a practical realization of the label, it has a size of about 20×50 mm and contains in its coat 4 a chlorine salt of the type indicated in a quantity of about 40–50 mg (dry weight). When the label is to be used, it is detached from the protective foil and fitted e.g. around one or more flower stalks with surfaces of the binder layer 3 stuck to one another or it is lowered down separately into the water.

The said barrier layer 5 in accordance with the present invention is constituted of a specially selected surface lacquer, which is based on at least one acrylic compound, and which is applied to the coat 4 of active material in the form of a mixture preferably containing several acrylic compounds and a photoinitiator which hardens the lacquer under the influence of UV-light. The mixture is applied appropriately in a quantity of 25–35 g/m$^2$ calculated on dry weight.

The surface lacquer proposed in accordance with the invention forms a barrier layer which reduces the risk of a release of the bactericidal and bacterial inhibiting agent, e.g. chlorine, in a moist environment. Furthermore, the risk of skin irritations in persons handling the labels is reduced as the agent cannot issue forth through the surface lacquer. The danger of the bactericidal and/or bacterial inhibiting agent coming into contact with clothing and damaging the same is also eliminated. This applies also to embodiments of the invention where the label is provided with passages. If e.g. during transport or storage of a bouquet, water accidentally should get onto the label kept therein, and the active agent chosen for the label is, for example, chlorine, little chlorine smell would develop. If the label is manipulated with wet hands, there is no risk of skin irritation either, since release of active substance through e.g. perforations occurs only after several minutes complete immersion in water.

The most tangible effect of the means in accordance with the invention, however, is that the release of the bactericidal and/or bacterial inhibiting agent in the water takes place over a longer period and in a more controllable manner than would be the case in labels of a similar type known hitherto. This is achieved by the material of the barrier layer not allowing water and bactericidal and/or bacterial inhibiting agent to pass through to an appreciable extent, but by these being released on the whole only via the regions which are not protected by barrier layers, e.g. one or more of the lateral edges of the label and any passages which have been provided in the surrounding layers. As a result of the regulated, and by comparison with previous technique greatly reduced, rate of release after immersion in the water, burning damages on the foliage, especially on sensitive species of flowers, encountered frequently on using e.g. chlorine according to previously applied techniques are avoided. Moreover, the flowers keep fresh for a longer time compared with flowers standing in water in which has been inserted a label which lacks a barrier layer.

Figure 3:
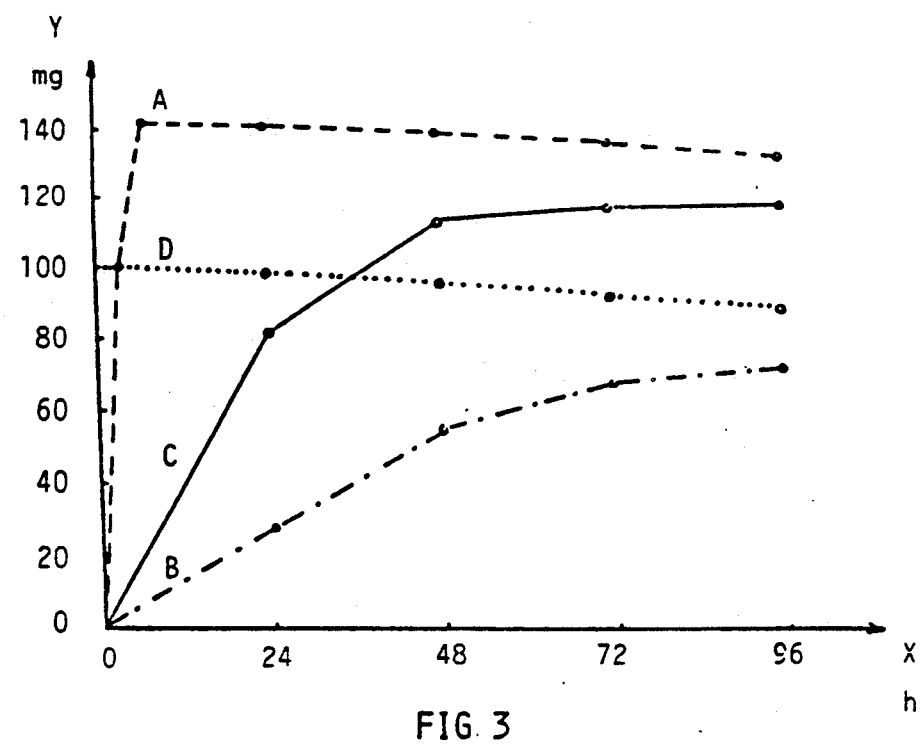

The technical effect of labels with or without barrier layer in accordance with the present invention is evident from the following experiments. In all these experiments the label was of the same size. Likewise identical were the quantity of active material, the quantity of water (1 liter) and the water temperature (24° C.). In all the experiments the carrier layer consisted of water-impermeable material and, more particularly, of polyvinyl chloride in a thickness of approximately 0.1 mm. The barrier layer consisted of an acrylic-based UV-lacquer (referred to hereinafter as UV 25-35) of a total thickness corresponding to 25-35 g/m$^2$ and containing several acrylic compounds and a photoinitiator which causes the lacquer to be set in approximately 1 s. The active substance consisted of sodium dichloroisocyanurate. The containers wherein the water was kept were adapted so as to minimize the discharge of chlorine to the environment. In FIG. 3 are indicated on the Y-axis the quantity in mg of chlorine released which is found in the water per liter water, and on the X-axis the time in hours.

EXPERIMENT 1

The experiment (cf. curve A) was intended to determine the rate of release of active substance from a label without a barrier layer, but whose carrier layer was water-impermeable. The curve indicates that after approximately 12 hours substantially all the chlorine had been released. Thereafter the chlorine content in the water diminished slowly owing to losses to the environment.

EXPERIMENT 2

A corresponding experiment (cf. curve B) was carried out with a label where the coat 4 with active material was covered on its upper side with a barrier layer which had no passages (corresponding to the embodiment described in connection with FIG. 1). The label, for the rest, was of the same dimensions and build-up as the label in experiment 1. The active material thus was accessible for contact with the water only along the transverse edge surfaces of the label. The quantity of chlorine in the water increased continuously during the 96 hours of the experiment. After 96 hours the increase was very moderate. It was found that only after approximately 36 hours the chlorine content was sufficiently high to achieve an inhibiting effect on the bacterial growth which would influence the life of the flowers. During the first 18 hours the bacterial growth continued substantially without any reduction.

EXPERIMENT 3

The barrier layer of the label was perforated, the perforations being distributed substantially uniformly over the surface of the barrier layer. For the rest the label corresponded to that which was used in experiment 2. It is evident from the result (curve C) that the quantity of chlorine released after 12 hours already corresponded to the quantity which had been released after 36 hours on using a barrier layer without holes. It is further evident from the curve that the total quantity of chlorine given off after 96 hours exceeds the quantity which has been given off by the label in experiment 2 and approaches the total quantity which is discharged by the label without a barrier layer.

The differences in the releasing effect are clearly evident. When the barrier layer is absent, the release takes place so rapidly that after approximately 6 hours all the chlorine in the active material has been released. With a barrier layer and without the provision of holes the chlorine is released very slowly from the active coat and not even after 96 hours attains an accumulated quantity corresponding to the quantity which is released from the label without a barrier layer. The explanation for this is that in the absence of a barrier layer all the active material in the coat 4 will be accessible for contact with water. By contrast it is found that the label in accordance with experiment 2 after 96 hours releases only a limited amount of chlorine which can be explained by the fact that chlorine is released from the coat only in a region close to the edges of the label, whereas the more centrally located material does not substantially release any chlorine. The width of the region of release at the edges of the label can be increased to a certain extent by raising the thickness of the coat 4 with active material which also brings about an increase in the rate of release during the first phase of the release process. On the other hand it takes such a long time for the water to release chlorine from the centrally situated material portions, that the contribution to the quantity of chlorine in the water which can be furnished from these regions is without real significance.

During the first phase of the release process the rate of release of the label provided with passages can be increased by increasing the number of passages (exposed surface on the coat 4 with active material) in the region nearest the edges of the label. In this way the release process can be directed so that the curve C is given a steeper gradient in the starting phase and a more gentle gradient thereafter. By reducing the exposed surface, e.g. The number of passages in the edge regions of the label it is possible instead to reduce the rate of release during the first part of the release process so that the curve C obtains the weaker gradient in the starting phase. After substantially all the accessible chlorine has been released from the edge region of the label, the subsequent supply of chlorine to the water takes place on the whole merely via the passages in the central portion of the label. It is obvious, therefore, that by providing a certain number and a certain defined layout of the passages in the barrier layer, a regulation of the rate of release in time, and thereby also a regulation of the amount of chlorine which is present in the vase water, will be achieved.

The effect described in the foregoing paragraph is obtained in an alternative embodiment through variation of the opening area of the passages. Through selection of the number of passages and/or the size of the passages the rate of release is thus controlled and in this way the rate of release and the accumulated quantity of chlorine can be varied in time so as to adapt to the tolerance different cut flowers present towards chlorine. Naturally the method is not limited to being applied only to the release of chlorine, but the method is generally applicable to the release of bactericidal and/or bacterial inhibiting agent from the coat 4 comprising active material.

In the diagram has also been included a curve D which indicates how chlorine has been discharged to the atmosphere during 96 hours if the quantity of chlorine at the start was 100 mg. The experiment was carried out under corresponding conditions as experiments 1-3 whereby the curve D also constitutes an indication of losses to the environment during experiments A-C. The slope of the curve D corresponds to a loss of approximately 3% chlorine per day. It should be noted that on application of the invention the amount of chlorine decreases more rapidly because of the reactions which ensue in the vase water between chlorine and substances and/or organisms occurring in the vase water.

The experiments were completed by placing a drop of pure water on a dry label and noting that a reagent powder for chlorine (N,N-diethyl-p-phenylenediamine sulphate) was instantly color red when the barrier layer was absent whilst it remained unaffected when a barrier layer without passages was in position. When a sprinkle of pure water was brought onto a dry label with UV-25-35 lacquer and a test with reagent powder carried out, no discharge of any chlorine could be detected, not even when the powder was rubbed in for a few minutes. This confirms that on the label in accordance with the present invention the barrier layer prevents chlorine from passing into the water.

EXPERIMENT 4

The effect of different preservative agents on cut flowers was examined. In each test five stalks were used in a vase with 0.5 liter of water. In the Table which follows the symbols used have the following meanings:
KONT = No preservative agent UV-N = Label without barrier layer and with carrier layer covered by an active coat containing sodium dichloroisocyanurate, this label being used jointly with two lumps of sugar.

UV-A = Label with barrier layer lacking passages and consisting of UV-25-35 lacquer comprising several (three) acrylic compounds and with sodium dichloroisocyanurate in the active layer, this label being used jointly with two lumps of sugar.

KRIS = Krislite, which is the trade name of another preservative agent and which is used in the specified quantity.

The quality of the cut flowers is assessed on a scale 0-5, where 5 is the highest quality.

TABLE

| Species | Treatment | Date of Assessment | | | | |
|---------|-----------|------|------|-------|-------|-------|
|         |           | 7/12 | 9/12 | 10/12 | 13/12 | 21/12 |
| Rose    | KONT      | 5    | 4    |       | 3     | 1     |
| Gabriela| UV-N      | 5    | 5    |       | 4     | 4*    |
|         | UV-A      | 5    | 5    |       | 5     | 5     |
|         | KRIS      | 5    | 5    |       | 4     | 3**   |
| Gerbera | KONT      | 5    | 3    |       | 3     | 0     |
|         | UV-N      | 5    | 5    |       | 1     | 0     |
|         | UV-A      | 5    | 5    |       | 3     | 0     |
|         | KRIS      | 5    | 5    |       | 3     | 0     |
| "Green" | KONT      | 5    | 5    | 1     | 0     | 0     |
| Adianthum | UV-N    | 5    | 2    | 0     | 0     | 0     |
|         | UV-A      | 5    | 3    | 3     | 2     | 0     |
|         | KRIS      | 5    | 2    | 0     | 0     | 0     |

*Green leaves wither
**Green leaves turn yellow

It is clearly evident from the above results that preservative agents have a beneficial effect on the presentation quality of the flowers and that UV-A (acrylic compound lacquer-label) in accordance with the invention) is superior to the label without barrier layer and, for certain flowers, is also better than the preservative agent called Krislite.

The active coat, beside containing a chlorine salt as a preservative, may include other active substances, such as other bactericides, one or more bacterial inhibiting substances, one or more surface-active substances and one or more nutrients. Examples of substances which in certain applications are included in the active coat by themselves or in combination are silver thiosulphate or compounds containing nickel, copper or aluminium.

A preferred UV-lacquer in accordance with the invention contains as acrylic compound components an acrylate derivative, hexanediol diacrylate, trimethylolpropane triacrylate and acrylo-epoxide derivative.

Acrylic lacquers of a diversity of compositions are able to be used. Examples of lacquers are those acrylic lacquers which contain photoinitiators of a composition which entails a hardening of the lacquer within a short time, as a rule within approximately 3 s, and preferably 1 s, when the lacquer is exposed to ultraviolet light exceeding a certain intensity.

It has been found appropriate to select as a barrier layer an acrylic compound which has been selected from the group consisting of acrylate derivatives, diacrylate derivatives, triacrylate derivatives and acrylo-epoxide compounds and to allow photoinitiators according to the above to enter into the lacquer.

In applications where passages are absent, experiments have shown that in certain compositions the coat 4, which includes the active material, rapidly sets free bactericidal agents immediately after immersion in the water, but that thereafter the discharge of agent becomes slower and gradually ceases altogether. This phenomenon is utilized in certain of the aforementioned applications of the invention in order to control the discharge of bactericidal and/or bacterial inhibiting agent in time through e.g. selective distribution of the layout of the passages in the barrier layer or of holes in the label. By the selection described earlier of the size of the passages or of the holes and the number of passages or holes per surface unit, the contact surfaces between water and active material are regulated, as a result of which the active material which is located away from the edges of the label or from the holes will continue to discharge bactericidal material, even after the discharge via the active material exposed at the edges of the label or at the holes has substantially ceased. In the region adjoining the passages too the depth of effectiveness in the active material for the penetrant water is limited. In certain applications the discharge of bactericidal and/or bacterial inhibiting agents directly after immersing the label into the water is accelerated by increasing the number of passages or holes and/or the size of the these passages or holes close to the edges of the label, whereas in other applications the supply of bactericidal and/or bacterial inhibiting agent is kept to a lower level by placing passages only in the central parts of the label.

One phenomenon occuring on application of a barrier layer which contains acrylic compound components and where the lacquer applied is hardened with the help of ultraviolet light, is that the lacquer easily wrinkles during hardening, a phenomenon which is particularly common in thick lacquer layers. Such a wrinkling frequently results in the lacquer layer becoming water-permeable. In accordance with the invention, therefore, the barrier layer is applied in several successive courses and the lacquer is allowed to harden between each course. In this way the lacquer is kept at such a thickness each time that wrinkling is avoided.

When using acrylic lacquers which contain photoinitiators a thickness corresponding to 25–35 g/m$^2$ is required so that the barrier layer after hardening prevents the passage of water.

The above description referred only to a limited number of embodiments of the invention, but it will be readily understood by those versed in the art that the invention encompasses a large number of embodiments within the scope of the subsequent claims.

What is claimed is:

1. An article for prolonging the life of cut flowers which are placed in water comprising a label adapted for placement in contact with water into which cut flowers are to be placed, said label including a carrier layer having upper and lower surfaces, a coat of material applied on the upper surface of the carrier layer, said coat of material containing an active material including at least one active substance for releasing bactericidal or bacterial inhibiting agents in the presence of water, and means including a water impermeable layer also impermeable to said agents for preventing contact of water thereof except for selective, discrete and limited regions of said coat of material and for preventing release of said agents from said coat of material into the water, said water-impermeable and agent-impermeable layer being juxtaposed with said coat of material in face to face relation on, and substantially covering, the surface of said coat material parallel to but not in contact with said carrier layer.

2. An article as claimed in claim 1 further comprising an adhesive layer on said lower surface of the carrier layer.

3. An article as claimed in claim 2 wherein at least one of said carrier layer and adhesive layer is non-permeable to water to constitute part of said means for preventing contact of water with said coat of material.

4. An article as claimed in claim 1 wherein said means leaves the side edges of said coat of material exposed.

5. An article as claimed in claim 1 wherein said water impermeable layer is provided with holes for passage of water to said coat of material.

6. An article as claimed in claim 5 wherein said holes are arranged in said water impermeable layer in a first group adjoining the edges thereof and a second group nearer the center of the water impermeable layer, said holes in the first group having a larger surface area than said holes in the second group.

7. An article as claimed in claim 11 wherein said active material is sodium dichloroisocyanurate.

8. An article as claimed in claim 1 wherein said water impermeable layer is constituted by a lacquer layer of a hardened acrylic compound selected from the group consisting of acrylate derivatives, diacrylate derivatives, triacrylate derivatives and acryloepoxides, said lacquer layer including a photo.initiator for intiating hardening of the lacquer layer under the influence of UV light.

9. An article as claimed in claim 8 wherein the acrylic compound is present in each layer in an amount of 25–35 g/m$^2$ calculated by dry weight.

10. An article as claimed in claim 8 wherein said water impermeable layer comprises a plurality of said lacquer layers which have been successively hardened to avoid wrinkling.

11. An article as claimed in claim 13 wherein said carrier layer is water permeable and said adhesive layer is water impermeable.

12. An article as claimed in claim 1 wherein said means provides controlled release of said agents to said cut flowers at a rate which prevents damage to the cut flowers and is substantially constant with respect to time.

13. An article for prolonging the life of cut flowers which are placed in water comprising a label adapted for placement in contact with water into which cut flowers are to be placed, said label including a carrier layer having upper and lower surfaces, a coat of material applied on the supper surface of the carrier layer, said coat of material containing an active material including at least one active substance for releasing bactericidal or bacterial inhibiting agents in the presence of water, and means including a water impermeable layer also impermeable to said agents for preventing contact of water with said coat of material over substantially the entire extent thereof except for selective, discrete and limited regions of said coat of material and for preventing release of said agents from said coat of material into the water, said water and agent impermeable layer being juxtaposed with said coat of material in face to face relation on, and substantially covering, the surface of said coat material parallel to but not in contact with said carrier layer and comprising a plurality of lacquer layers including a photoinitiator for initiating hardening of said lacquer layers under the influence of UV light, said plurality of lacquer layers being successively hardened to avoid wrinkling of said water impermeable layer.

14. An article as claimed in claim 13 wherein each lacquer layer comprises a hardened acrylic compound.

15. An article as claimed in claim 13 wherein the acrylic compound is present in each layer in an amount of 25-35 g/m² calculated by dry weight.

16. An article as claimed in claim 13 wherein said lacquer layer contains an acrylic compound selected from the group consisting of hexanediol diacrylate, trimethylolpropane triacrylate and acrylo-epoxide derivatives.

17. An article as claimed in claim 1 wherein said active substance is constituted to release, as said agents, a chlorine containing composition.

18. An article as claimed in claim 6 wherein a greater number of holes are provided in said first group than in said second group.

* * * * *